United States Patent [19]

Gaignault et al.

[11] 4,005,206
[45] Jan. 25, 1977

[54] [9H]-PYRIDO-[3,4-b]-INDOLES

[75] Inventors: Jean-Cyr Gaignault; Jean Vacher; Daniel Frechet, all of Paris, France

[73] Assignee: Roussel-UCLAF, Paris, France

[22] Filed: Apr. 7, 1976

[21] Appl. No.: 674,415

[52] U.S. Cl. .......................... 424/263; 260/240.4; 260/326.15; 260/326.16; 260/326.13 R; 260/296 A
[51] Int. Cl.² ..................................... C07D 401/14
[58] Field of Search ................ 260/296 A; 424/263

*Primary Examiner*—Henry R. Jiles
*Assistant Examiner*—Robert T. Bond
*Attorney, Agent, or Firm*—Hammond & Littell

[57] ABSTRACT

Novel 1,2,3,4-tetrahydro-[9H-pyrido-[3,4-b]-indoles of the formula

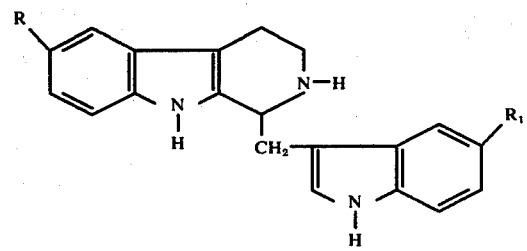

wherein R and $R_1$ are individually selected from the group consisting of hydrogen, halogen, hydroxy, alkoxy of 1 to 5 carbon atoms and benzyloxy with the proviso that $R_1$ is not hydroxy when R is halogen, alkoxy or benzyloxy and their non-toxic, pharmaceutically acceptable acid addition salts having tranquillizing properties and their preparation.

13 Claims, No Drawings

[9H]-PYRIDO-[3,4-B]-INDOLES

OBJECTS OF THE INVENTION

It is an object of the invention to provide the novel [9H]-pyrido-[3,4-b]-indoles of formula I and their non-toxic, pharmaceutically acceptable acid adddition salts and a process for their preparation as well as novel intermediates.

It is another object of the invention to provide novel tranquillizing compositions and to provide a novel method of tranquillizing warm-blooded animals.

These and other objects and advantages of the invention will become obvious from the following detailed description.

THE INVENTION

The novel compounds of the invention are selected from the group consisting of [9H]-pyrido-[3,4-b]-indoles of the formula

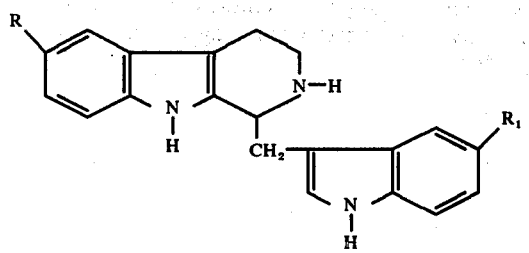

wherein R and $R_1$ are individually selected from the group consisting of hydrogen, halogen, hydroxy, alkoxy of 1 to 5 carbon atoms and benzyloxy with the proviso that $R_1$ is not hydroxy when R is halogen, alkoxy or benzyloxy and their non-toxic, pharamceutically acceptable acid addition salts.

Examples of suitable substituents for R and $R_1$ are hydrogen, hydroxy, halogen such as fluorine, chlorine or bromine, benzyloxy or alkoxy such as methoxy, ethoxy, propoxy, butoxy, sec-butoxy or tert.-butoxy.

Examples of non-toxic, pharmaceutically acceptable acids for the preparation of the acid addition salts are inorganic acids such as hydrochloric acid, hydrobromic acid, hydroiodic acid, nitric acid, sulfuric acid or phosphoric acid or organic acids such as acetic acid, formic acid, benzoic acid, maleic acid, fumaric acid, succinic acid, tartaric acid, citric acid, oxalic acid, glyoxylic acid, aspartic acid or alkane sulfonic acids such as methane sulfonic acid or aryl sulfonic acids such as benzene sulfonic acid.

Among the preferred compounds of formula I are those where R and $R_1$ are individually hydrogen, chlorine, hydroxy, methoxy or benzyloxy with the proviso that $R_1$ is not hydroxy where R is chlorine, methoxy or benzyloxy and their non-toxic pharmaceutically accceptable acid addition salts. Specific derivatives are 1-(5'-methoxy-3'-indolyl-methyl)-6-methoxy-1,2,3,4-tetrahydro-[9H]-pyrido-[3,4-b]-indole and its hydrochloride; 1-(5'-methoxy-3'-indolyl methyl)-1,2,3,4-tetrahydro-[9H]-pyrido-[3,4-b]-indole and its hydrochloride; 6-hydroxy-1-(3'-indolylmethyl)-1,2,3,4-tetrahydro-/9H/-pyrido-/3,4-b/-indole and its fumarate; 6-chloro-1-(3'-indolyl methyl)-1,2,3,4-tetrahydro-[9H]-pyrido-[3,4-b]-indole and its hydrochloride and 1-(5'-hydroxy-3'-indolyl methyl)-1,2,3,4-tetrahydro-[9H]-pyrido-[3,4-b]-indole and its hydrochloride.

The novel process of the invention for the preparation of compounds of formula I wherein R is defined as above and $R_1$ is hydrogen, halogen, alkoxy of 1 to 5 carbon atoms or benzyloxy comprises reacting a tryptamine of the formula

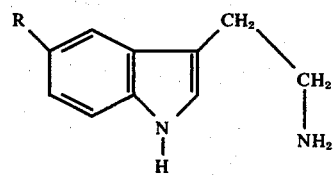

with a 3-indole pyruvic acid of the formula

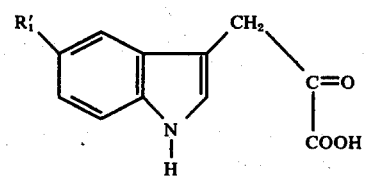

wherein $R_1'$ is selected from the group consisting of hydrogen, halogen, alkoxy of 1 to 5 carbon atoms and benzyloxy to obtain a compound of the formula

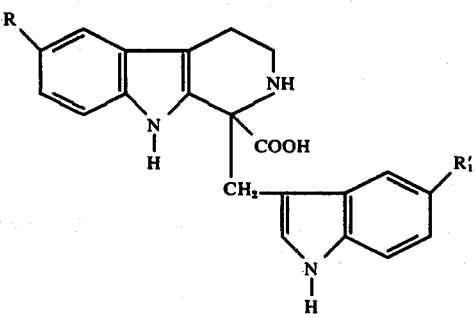

and decarboxylating the latter to form the corresponding compound of formula I wherein $R_1$ is hydrogen, halogen, alkoxy of 1 to 5 carbon atoms or benzyloxy which may be treated with an acid to form the corresponding non-toxic, pharmaceutically acceptable acid addition salt.

Preferably, the reaction of the tryptamine of formula II with the 3-indole-pyruvic acid of formula III is effected in aqueous or anhydrous media, optionally in the presence of a low molecular weight alcohol such as butanol at a temperature between 50° C and the reflux temperature for 48 hours to 7 days. The decarboxylation of the compound of formula IV is effected by heating for several hours in the presence of a strong mineral acid such as hydrochloric acid. When R of the compound of formula I is hydroxy, the R of the compound of formula II is hydroxy and this latter is used in the form of a complex with creatinine sulfate.

A variation of the process when R is hydrogen or benzyloxy and $R_1$ benzyloxy or R is hydrogen or hydroxy and $R_1$ is hydroxy comprises reacting a tryptamine of the formula

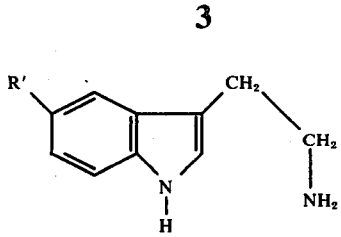

wherein R' is hydrogen or benzyloxy with a product of the formula

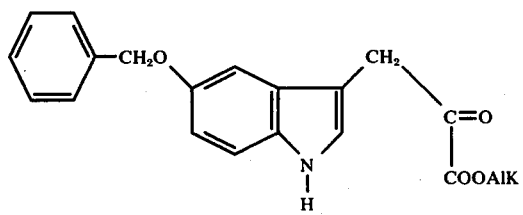

wherein AlK is alkyl of 1 to 3 carbon atoms to form a compound of the formula

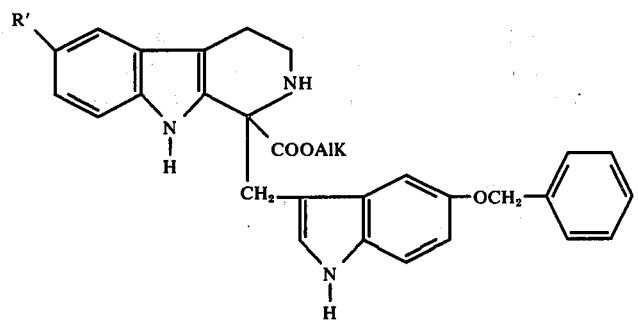

which is then hydrolyzed and decarboxylated to form a compound of the formula

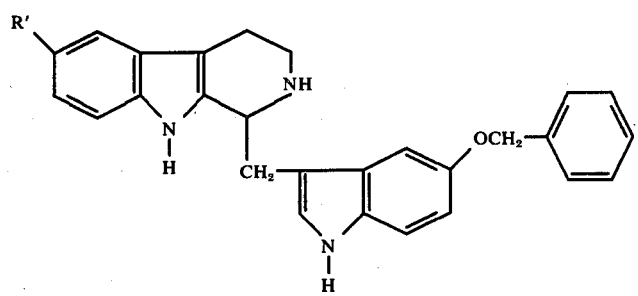

which may be recovered per se or as its non-toxic, pharmaceutically acceptable acid addition salt or may be subjected to hydrogenolysis to obtain a compound of formula I wherein R is hydrogen or hydroxy and $R_1$ is hydroxy which may be isolated per se or as its non-toxic, pharmaceutically acceptable acid addition salt.

Preferably, the tryptamine of formula II' and the compound of formula V reaction is effected in a low molecular weight alkanol such as ethanol at a temperature of 50° C to the reflux temperature for 48 hours to 7 days and the decarboxylation is effected with an alkali metal hydroxide such as sodium hydroxide or potassium hydroxide in a low molecular weight alcohol such as ethanol at the reflux temperature. The hydrogenolysis may be effected with gaseous hydrogen in the presence of a catalyst such as palladium or platinium on charcoal. This process is preferred when preparing compounds of formula I wherein $R_1$ is benzyloxy.

When it is desired to form the acid addition salts, the free base of formula I and the acid are reacted in approximately stoichiometric proportions and the said salts may be prepared without isolation of the base.

The novel tranquillizing compositions of the invention are comprised of an effective amount of at least one compound of formula I or their non-toxic, pharmaceutically acceptable acid addition salts and a pharmaceutical carrier. The compositions may be in the form of tablets, dragees, gelules, granules, suppositories or injectable solutions or suspensions made in the usual manner.

The compositions may be prepared by incorporating the active compound in the usual excipients used for pharmaceutical compositions such as talc, arabic gum, lactose, starch, magnesium stearate, cacao butter, aqueous and non-aqueous vehicles, fatty bodies of animal or vegetable origin, paraffinic derivatives, glycols, preservatives or diverse wetting agents, dispersants or emulsifiers.

The compositions have remarkable tranquillizing properties and some of the products possess antagonistic properties to serotonine and to platelet aggregation caused by collagen. The compositions may be used for treatment of anxiety, hyperemotivity, psychomotric agitation, irritability, sleeping problems, various migraines and related vasomotric headaches.

The novel method of the invention for tranquillizing warm-blooded animals, including humans, comprises administering to warm-blooded animals a tranquillizing effective amount of at least one compound of formula I or its non-toxic, pharmaceutically acceptable acid addition salt. The compound may be administered orally, rectally or parenterally and the usual useful dose is 0,1 to 2 mg/kg. The method is also useful as an antimigraine agent.

The compounds of formula III wherein $R_1'$ is halogen or alkoxy of 1 to 5 carbon atoms when they are not known, may be prepared by condensing a compound of the formula

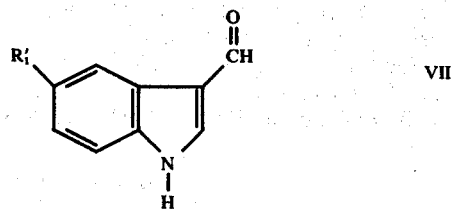

wherein $R_1'$ has the above definition with hydantoin to obtain a compound of the formula

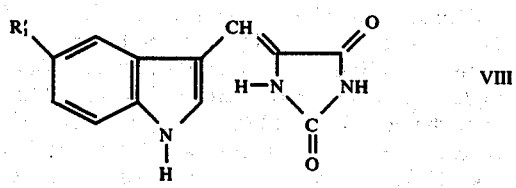

which is subjected to alkaline hydrolysis to obtain the corresponding compound of formula III.

The products of formula V wherein AlK is alkyl of 1 to 3 carbon atoms may be prepared by condensing the methyl ester of 5-benzyloxy-3-indolyl-acetic acid with an alkyl oxalate to obtain a compound of the formula

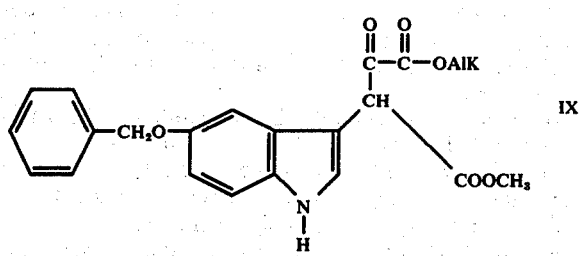

wherein AlK is as above and hydrolyzing and decarboxylating the latter to form the compound of formula V.

The compounds of formula VIII wherein $R_1$ is halogen, hydroxy or alkoxy of 1 to 5 carbon atoms and 5-chloro-3-indole-pyruvic acid are novel intermediates.

In the following examples there are described several preferred embodiments to illustrate the ivention. However, it should be understood that the invention is not intended to be limited to the specific embodiments.

EXAMPLE 1

1-(5'-methoxy-3'-indolyl-methyl)-6-methoxy-1,2,3,4-tetrahydro[9H]-pyrido-[3,4-b]-indole-hydrochloride 3.7 g of 5-methoxy-3-indole-pyruvic acid were added under a nitrogen atmosphere to a mixture of 2.74 g of 5-methoxy-tryptamine and 14.4 ml of N hydrochloric acid in 70 ml of n-butanol and after heating the mixture with stirring at 95° C for 48 hours, 7 ml of concentrated hydrochloric acid were added thereto. The mixture was stirred for 5 hours at 95° C and was then distilled to dryness under reduced pressure to obtain 7 g of raw product. The said product was chromatographed over silica gel and was eluted with an 8—2 chloroform-methanol mixture to obtain 2.7 g of product which was crystallized from 10 ml of ethyl acetate. The mixture was vacuum filtered and the 2 g of product were dissolved in 40 ml of methanol. The mixture was filtered and 40 ml of ethyl acetate were added to the filtrate. The mixture was concentrated to 30 ml and was vacuum filtered to obtain 1.55 g of 1-(5'-methoxy-3'-indolyl-methyl)-6-methoxy-1,2,3,4-tetrahydro-[9H]-pyrido-[3,4-b]-indole-hydrochloride in the form of white crystals melting at 225°–230° C.

Analysis: $C_{22}H_{23}N_3O_2$. HCl; molecular weight = 397.89; Calculated: %C, 66.41; %H, 6.08; %N, 10.56; %Cl, 8.91. Found: %C, 66.1; %H, 6.1; %N, 10.3; %Cl, 8.9.

EXAMPLE 2

1-(5'-methoxy-3'-indolyl-methyl)-6-hydroxy-1,2,3,4-tetrahydro[9H]-pyrido-[3,4-b]-indole A mixture of 10 g of 5-methoxy-3-indole-pyruvic acid, 14.7 g of serotonine-creatine sulfate, 150 ml of n-butanol and 150 ml of water was heated with stirring at 100° C for 5 days and after the addition of 30 ml of concentrated hydrochloric acid, the mixture was stirred for 5 hours at 100° C. The mixture was evaporated to dryness under reduced pressure and the 27 g of raw product were chromatographed over silica gel. Elution with a 7—3 chloroform-methanol mixture yielded 6 g of product which was dissolved in 160 ml of water at 80° C. The mixture was filtered and the filtrate was cooled and neutralized with sodium bicarbonate. After standing for 15 hours, the mixture was vacuum filtered to obtain 3.9 g of 1-(5'-methoxy-3'-indolyl-methyl)-6-hydroxy-1,2,3,4-tetrahydro-([9H]-pyrido-[3,4-b]-indole which after crystallization from methanol occurred as yellow crystal melting at about 170° C.

Analysis: $C_{21}H_{21}N_3O_2$; molecular weight = 347.40: Calculated: %C, 72.60; %H, 6.09; %N, 12.10. Found: %C, 72.6; %H, 6.0; %N, 12.1.

EXAMPLE 3

1-(3'-indolyl methyl)-6-methoxy-1,2,3,4-tetrahydro-[9H]-pyrido-[3,4-b]-indole hydrochloride 15.3 g of 3-indole-pyruvic acid were added under a nitrogen atmosphere to a solution of 14.3 g of 5-methoxy tryptamine, 100 ml of water, 75 ml of N hydrochloric acid and 75 ml of n-butanol and the mixture was heated with stirring at 100° C for 54 hours. 25 ml of concentrated hydrochloric acid were added to the mixture and after stirring for 2½hours at 100° C, the mixture was evaporated to dryness under reduced pressure. The 32 g of raw product were chromatographed over silica gel and elution was with a 7—3 chloroform-methanol mixture to obtain 10 g of product. The said product was crystallized from 30 ml of ethyl acetate and was vacuum filtered to obtain 8.8 g of product which were dissolved in 140 ml of methanol. The solution was filtered and 150 ml of ethyl acetate were added thereto. The mixture was concentrated and vacuum filtered to obtain 7.8 g of 1-(3'-indolyl methyl)-6-methoxy-1,2,3,4-tetrahydro-[9H]-pyrido-[3,4-b]-indole hydrochloride in the form of yellow crystals melting at about 250° C.

Analysis: $C_{21}H_{21}N_3O$ . HCl; molecular weight = 367.87: Calculated: %C, 68.56; %H, 6.03; %N, 11.42; %Cl, 9.64. Found: %C, 68.3; %H, 6.1; %N, 11.7; %Cl, 9.8.

EXAMPLE 4

1-(5'-chloro-3'-indolyl-methyl)-1,2,3,4-tetrahydro-[9H]-pyrido-[3,4-b]-indole hydrochloride STEP A: 5-chloro-3-indole-pyruvic acid A mixture of 23.8 g of 5-chloro-3-formyl-indole, 13.2 g of hydantoin and 25 ml of piperidine was heated with stirring under a nitrogen atmosphere in a bath at 135° C for 30 minutes and 50 ml of water and 25 ml of acetic acid were added thereto. The mixture was cooled and vacuum filtered to obtain 30.8 g of product which was used as is for the next step.

A mixture of 30.8 g of said product and 700 ml of a solution containing 20 g of sodium hydroxide per 100 ml of water was refluxed with stirring under a nitrogen atmosphere for 5 hours and the mixture was cooled and extracted with ether. The aqueous phase was acidified with concentrated hydrochloric acid and the precipitate formed was extracted with ethyl acetate. The extracts were dried over magnesium sulfate, filtered and evaporated to dryness under reduced pressure to obtain 8.7 g of 5-chloro-3indole-pyruvic acid in the form of yellow crystals melting at about 180° C.

STEP B: 1-(5'-chloro-3'-indolyl-methyl)-1,2,3,4-tetrahydro[9H]-pyrido-[3,4-b]-indole-hydrochloride A solution of 9.5 g of 5-chloro-3-indole-pyruvic acid, 7.8 g of tryptamine hydrochloride, 50 ml of water and 50 ml of n-butanol under a nitrogen atmosphere was heated with stirring to 100° C for 55 hours and after the addition of 10 ml of concentrated hydrochloric acid, the mixture was stirred at 100° C for 4 more hours. The mixture was evaporated to dryness under reduced pressure and the product was crystallized from 50 ml of isopropanol and was vacuum filtered to obtain 4 g of a product melting at 270° C. The mother liquor was chromatographed over silica gel and elution with a 7—3 chloroform-methanol mixture yielded 3 g of product which upon crystallization from isopropanol yielded 2.2 g of 1-(5'-chloro-3'-indolyl-methyl-1,2,3,4-tetrahydro[9H]pyrido [3,4-] indole melting at 270° C. The said product and the 4 g of previous product were dissolved in 600 ml of refluxing methanol and the solution was filtered. The filtrate was concentrated to 100 ml and after the addition of 300 ml of methylene chloride, the mixture was concentrated to 100 ml. The mixture was vacuum filtered to obtain 4.2 g of 1-(5'-chloro-3'-indolyl methyl)-1,2,3,4-tetrahydro[9H-]pyrido-[3,4-]-indole-hydrochloride as colorless crystals melting at about 270° C.

Analysis: $C_{20}H_{18}ClN_3$ . HCl; molecular weight = 372.28: Calculated: %C, 64.52; %H, 5.14; %Cl, 19.05; %N, 11.29. Found: %C, 64.5; %H, 5.4; %Cl, 19.1; %N, 11.2.

EXAMPLE 5

1-(5'-methoxy-3'-indolyl-methyl)-1,2,3,4-tetrahydro-[9H]pyrido-[3,4-b]-indole-hydrochloride A mixture of 8.6 g of tryptamine hdyrochloride, 10.2 g of 5-methoxy-3-indole-pyruvic acid and 370 ml of water were heated with stirring under a nitrogen atmosphere for 64 hours at 100° C and then 37 ml of concentrated hydrochloric acid were added thereto. The mixture was heated for another 5 hours at 100° C and was then distilled to dryness under reduced pressure to obtain 21 g of raw product. The product was chromatographed over silica gel and was eluted with a 7—3 chloroform-methanol mixture to obtain 5.8 g of product. The latter was crystallized from isopropanol and was vacuum filtered to obtain 3.2 g of 1-(5'-methoxy-3'-indolyl methyl)-1,2,3,4-tetrahydro-[9H]-pyrido-[3,4-]-indole-hydrochloride which after successive crystallization from isopropanol, a 50—50 methanol-ethyl acetate mixture and isopropanol occured as colorless crystals melting at 270° C.

Analysis: $C_{21}H_{21}N_3O$ . HCl; molecular weight = 367.87: Calculated: %C, 68.56; %H, 6.03; %N, 11.42; %Cl, 9.64. Found: %C, 68.8; %H, 6.1; %N, 11.1; %Cl, 9.6.

EXAMPLE 6

6-hydroxy-1-(3'-indolyl-methyl)-1,2,3,4-tetrahydro [9H]pyrido-[3,4-b]-indole-fumarate STEP A: 6-hydroxy-1-(3'-indolyl-methyl)-1,2,3,4-tetrahydro[9H] pyrido-[3,4-b]-indole A mixture of 15 g of 3-indole-pyruvic acid, 24 g of creatinine sulfate of 5-hydroxy-tryptamine, 150 ml of water and 150 ml of n-butanol was heated with stirring under a nitrogen atmosphere at 90° C for 68 hours and after the addition of 30 ml of concentrated hydrochloric acid thereto, the mixture was stirred for 5 hours at 100° C. The mixture was evaporated to dryness under reduced pressure to obtain 42 g of raw product which was chromatographed over silica gel. Elution with a 7—3 chloroform-methanol mixture yielded 12 g of product which was dissolved in 1000 ml of refluxing water. The solution was filtered, cooled and made alkaline by addition of sodium bicarbonate. The precipitate formed was extracted with ethyl acetate and the extracts were dried over magnesium sulfate, filtered and evaporated to dryness under reduced pressure to obtain 7 g of 6-hydroxy-1-(3'-indolyl-methyl)-1,2,3,4-tetrahydro-[9H]-pyrido-[3,4-b]-indole in the form of a brown oil.

STEP B: 6-hydroxy-1-(3'-indolyl-methyl)-1,2,3,4-tetrahydro[9H] pyrido-[3,4-b]-indole-fumarate A solution of 2.56 g of fumaric acid in a minimum amount of methanol was added dropwise to a solution of 7 g of 6-hydroxy-1-(3'-indolyl methyl)-1,2,3,4-tetrahydro [9H] pyrido[3,4-] indole in 50 ml of isopropanol and the mixture was vacuum filtered to obtain 7 g of product which was crystallized from methanol to obtain 3.5 g of 6-hydroxy-1-(3'-indolyl methyl)-1,2,3,4-tetrahydro-[9H]-pyrido-[3,4-b]-indole-fumarate in the form of colorless crystals melting at about 270° C.

Analysis: $C_{20}H_{19}N_3O$ . $C_4H_4O_4$; molecular weight = 433.45: Calculated: %C, 66.50; %H, 5.35; %N, 9.70. Found: %C, 66.3; %H, 5.4; %N, 9.6.

EXAMPLE 7

6-chloro-1-(3'-indolyl methyl)-1,2,3,4-tetrahydro-[9H]-pyrido-[3,4-b]-indole 13 g of 3-indole pyruvic acid were added over 4 days under a nitrogen atmosphere to a solution of 10 g of 5-chloro-tryptamine hydrochloride in 200 ml of water with 4 g being initially added, 2 g being added after 8 hours, 2 g added after 24 hours, 2 g added after 2 days, 2 g added after 3 days and 1 g added after 4 days. The mixture was then stirred at 100° C for 6 days and after the addition of 20 ml of concentrated hydrochloric acid, the mixture was heated for 5 hours at 110° C. The mixture was evaporated to dryness under reduced pressure to obtain 26 g of raw product which was chromatographed over silica gel. Elution with a 7—3 chloroform-methanol mixture yielded 10 g of product which was chromatographed again under the same conditions. The resulting product was crystallized from ethyl acetate to obtain 2.3 g of 6-chloro-1-(3'indolyl methyl)-1,2,3,4-tetrahydro-[9H]-pyrido-[3,4-b]-indole-hydrochloride which after crystallization from isopropanol melted at 255° C.

2.6 g of the said product were dissolved in 400 ml of water at 80° C and the solution was filtered and made alkaline with sodium bicarbonate. The mixture was vacuum filtered and the filtrate was evaporated to dryness under reduced pressure to obtain 2 g of 6-chloro-1-(3'-indoyl methyl)-1,2,3,4-tetrahydro-[9H]-pyrido-[3,4-b]-indole melting at 120° C.

Analysis: $C_{20}H_{18}ClN_3$; molecular weight = 355.82: Calculated: %C, 71.53; %H, 5.40; %N, 12.51; %Cl, 10.56. Found: %C, 71.4; %H, 5.6; %N, 12.7; %Cl, 10.9.

EXAMPLE 8

1-(5'-benzyloxy-3'-indolyl-methyl)-1,2,3,4-tetrahydro-[9H]-pyrido-[3,4-b]-indole-hydrochloride STEP A: ethyl 5-benzyloxy-α-methoxycarbonyl-3-indole-pyruvate A mixture of 2.55 g of sodium in 80 ml of absolute ethanol was stirred at room temperature until the sodium dissolved and then 16.1 g of ethyl oxalate were added thereto all at once. The mixture was stirred at room temperature for 5 minutes and then a solution of 29.5 g of methyl 5-benzyloxy-3-indole-acetate in 150 ml of anhydrous ether was added thereto over 15 minutes. The mixture was stirred for 3 hours at room temperature and after 600 ml of water were added, the neutral fraction of the mixture was extracted with ether. The aqueous phase was acidified with concentrated hydrochloric acid and was then extracted with methylene chloride. The extracts were dried over magnesium sulfate, filtered and evaporated to dryness under reduce pressure to obtain 33.2 g of ethyl 5-benzyloxy-α-methoxycarbonyl-3-indole-pyruvate in the form of a brown oil which was used as is for the next step.

STEP B: ethyl 5-benzyloxy-3-indole-pyruvate

A solution of 14.8 g of ethyl 5-benzyloxy-α-methoxycarbonyl-3-indole-pyruvate in 7.5 ml of water and 75 ml of acetic acid was refluxed for 4¼ hours and was then evaporated to dryness under reduced pressure. The residue was taken up in benzene and the mixture was vacuum filtered to obtain 3.1 g of ethyl 5-benzyloxy-3-indole-pyruvate as a beige product which melted at 169°-170° C after crystallization from ether. Thin layer chromatography after crystallization from ether showed the presence of ethyl 5-benzyloxy-3-indole-pyruvate (Rf = 0.70) and 5-benzyloxy-3-indole-pyruvic acid (Rf = 0.15).

STEP C: ethyl 1-(5'-benzyloxy-3'-indolyl methyl)-1,2,3,4-tetrahydro-1-[9H]-pyrido-[3,4-b]-indole carboxylate A mixture of 233 mg of ethyl 5-benzyloxy-3-indole-pyruvate and 333 mg of tryptamine hydrochloride in 23 ml of absolute ethanol was refluxed with stirring for 5 days and was then evaporated to dryness under reduced pressure. The residue was chromatographed over silica gel and elution with a 9—1 chloroform-methanol mixture yield 320 mg of an amorphous product with an Rf = 0.65. The product was crystallized from a minimum of ether and the mixture was vacuum filtered. The solid product was washed with isopropyl ether and was crystallized from isopropyl ether to obtain 225 mg of ethyl 1-(5'-benzyloxy-3'-indolyl-methyl)-1,2,3,4-tetrahydro-1-[9H]-pyrido-[3,4-b]-indole-carboxylate in the form of clear yellow crystals melting at 120°-125° C (melts slowly towards 75°- 80° C)

Analysis: $C_{30}H_{29}N_3O_3$; molecular weight = 479.56: Calculated: %C, 75.13; %H, 6.10; %N, 8.76. Found: %C, 75.2; %H, 6.4; %N, 8.9.

STEP D: 1-(5'-benzyloxy-3'-indolyl methyl)-1,2,3,4,-tetrahydro-[9H]-pyrido-[3,4-b]-indole-hydrochloride A mixture of 4.8 g of 1-(5'-benzyloxy-3'-indolyl methyl)-1,2,3,4-tetrahydro-1-[9H]-pyrido-[3,4-b]-indole-carboxylate, 150 ml of ethanol and 20 ml of N sodium hydroxide was refluxed with stirring for 45 minutes and after the addition of 5 ml of concentrated hydrochloric acid, the mixture was refluxed for 5 hours and then was evaporated to dryness under reduced pressure. The 5.1 g of raw product were crystallized from isopropyl ether and was vacuum filtered to obtain 3.5 g of 1-(5'-benzyloxy-3'-indolyl methyl)-1,2,3,4-tetrahydro-[9H]-pyrido-3,4-b]-indole-hydrochloride in the form of beige crystals melting at 270°-280° C.

Analysis: $C_{27}H_{25}N_3O$. HCl; molecular weight = 443.96: Calculated: %C, 73.04; %H, 5.90; %N, 9.46; %Cl, 7.99. Found: %C, 73.0; %H, 5.9; %N, 9.4; %Cl, 8.1.

EXAMPLE 9

1-(5'-hydroxy-3'-indolyl-methyl)-1,2,3,4-tetrahydro-[9H]-pyrido-[3,4-b]-indole-hydrochloride 2.3 of 10% palladized carbon were added to a suspension of 4.6 g of 1-(5'-benzyloxy-3'-indolyl methyl)-1,2,3,4-tetra-hydro-[9H]-pyrido-[3,4-b]-indole-hydrochloride in 460 ml of absolute ethanol and hydrogen was bubbled therethrough with stirring for 5 hours during which 200 ml of hydrogen were absorbed. The mixture was filtered and the filter was rinsed with ethanol and then methanol. The filtrate was evaporated to dryness to obtain 3.7 g of raw product which was crystallized from ethyl acetate and vacuum filtered to obtain 3.4 g of 1-(5'-hydroxy-3'-indolyl methyl)-1,2,3,4-tetrahydro-[9H]-pyrido-[3,4-b]-indole-hydrochloride which after crystallization from methanol occured as clear beige crystals melting at 280° C.

Analysis: $C_{20}H_{19}N_3O$ .HCl; molecular weight = 353.84: Calculated: %C, 67.88; %H, 5.70; %N, 11.87; %Cl, 10.02. Found: %C, 67.8; %H, 5.7; %N, 11.6; %Cl, 10.2.

EXAMPLE 10

1-(5'-benzyloxy-3'-indolyl methyl)-6-benzyloxy-1,2,3,4-tetrahydro-[9H]-pyrido-[3,4-b]-indole-hydrochloride STEP A: ethyl 1-(5'benzyloxy-3'-indolyl-methyl)-6-benzyloxy-1,2,3,4-tetrahydro-1-[9H]-pyrido-[3,4-b]-indole-carboxylate An ethyl acetate solution saturated with hydrochloric acid was added to a solution of 10 g of 5-benzyloxy-tryptamine in 200 ml of isopropanol until the pH was 1–2 and the mixture was vacuum filtered. The crystals were washed with ethyl acetate and dried under reduced pressure to obtain 11.3 g of 5-benzyloxy-tryptamine hydrochloride melting at 250° C.

A mixture of 9 g of ethyl 5-benzyloxy-3-indole-pyruvate and 9 g of 5-benzyloxy tryptamine hydrochloride in 250 ml of absolute ethanol was refluxed with stirring for 3 days and was then evaporated to dryness under reduced pressure. The 17 g of residue was chromatographed over silica gel and was eluted with a 9–1 chloroform-methanol mixture to obtain 12 g of raw product. The latter was dissolved in ether and the solution was treated with activated carbon, filtered and subjected to crystallization to obtain 10.3 g of 1-(5'-benzyloxy-3'-indolyl methyl)-6-benzyloxy-1,2,3,4-tetrahydro-1-[9H]-pyrido-[3,4-b]-indole-carboxylate as a beige solid melting at 125° C.

Analysis: $C_{37}H_{35}N_3O_4$; molecular weight = 585.67: Calculated: %C, 75.87; %H, 6.02; %N, 7.18. Found: %C, 75.8; %H, 5.8; %N, 6.8.

STEP B: 1-(5'-benzyloxy-3'-indolyl-methyl)-6-benzyloxy-1,2,3,4-tetrahydro-[9H]-pyrido-[3,4-b]-indole-hydrochloride A suspension of 10.3 g of 1-(5'-benzyloxy-3'-indolyl-methyl)-6-benzyloxy-1,2,3,4-tetrahydro-1-[9H]-pyrido-[3,4-b]-indole-carboxylate, 34 ml of N sodium hydroxide and 103 ml of ethanol was refluxed for 30 minutes with stirring and 9.7 ml of concentrated hydrochloric acid were added thereto all at once. The mixture was refluxed for 6 hours and then was cooled and vacuum filtered. The filter was washed with water and then ethanol to obtain 8.3 g of raw product. The product was dissolved in 2 liters of refluxing methanol and then 1000 ml of water were added. The mixture was filtered and the filtrate was concentrated to 400 ml and stood overnight. The mxture was vacuum filtered and the filtrate was washed with water and evaporated to dryness under reduced pressure to obtain 6.9 g of 1-(5'-benzyloxy-3'-indolyl-methyl)-6-benzyloxy-1,2,3,4-tetrahydro-[9H]-pyrido-[3,4-b]-indole-hydrochloride in the form of clear yellow crystals melting at 252°–254° C.

Analysis: $C_{34}H_{31}N_3O_2 \cdot HCl$; molecular weight = 550.08: Calculated: %C, 74.23; %H, 5.86; %N, 7.64; %Cl, 6.45. Found: %C, 74.1; %H, 5.9; %N, 7,4; %Cl, 6.3.

EXAMPLE 11

1-(5'-hydroxy-3'-indolyl-methyl)-6-hydroxy-1,2,3,4-tetrahydro-[9H]-pyrido-[3,4-b]-indole-hydrochloride 1.5 g of 10% palladized carbon was washed 3 times with 20 ml of 0.5 N hydrochloric acid and then 4 times with 50 ml of water and 4 times with 50 ml of methanol, 300 ml of anhydrous methanol and then 3 g of the product of Example 10 were added and hydrogen was passed therethrough with stirring for 1 hour during which 260 cc of hydrogen were absorbed. The mixture was filtered into a round bottom flask containing a trace of butyl hydroxyanisole and the filter was rinsed with methanol. The filtrate was evaporated to dryness under reduced pressure to obtain 2g of 1-(5'-hydroxy-3'-indolyl methyl)-6-hydroxy-1,2,3,4,-tetrahydro-[9H]-pyrido-[3,4-b]-indole-hydrochloride in the form of a rose powder melting at about 250° C and the product was stored under an inert gas.

EXAMPLE 12

Tablets were prepared comprised of 5 mg of 1-(5'-methoxy-3'-indolyl methyl)-6-methoxy-1,2,3,4-tetrahydro-[9H]-pyrido-[3,4-b]-indole-hydrochloride, 1-(5'-methoxy-3'-indolyl methyl)-1,2,3,4-tetrahydro-[9H]-pyrido-[3,4-b]-indole-hydrochloride or 1-(5'-hydroxy-3'-indolyl methyl)-1,2,3,4-tetrahydro-[9H]-pyrido-[3,4-b]-indole-hydrochloride and sufficient excipient of lactose, starch, talc and magnesium stearate to obtain a final weight of 100 mg.

PHARMACOLOGICAL DATA

A. Tranquillizing properties

1. Antagonism toward amphetamine type

The antagonism of the compounds with regard to amphetaminic group was studied on groups of 10 male mice which received intraperitoneally 15 mg/kg of dexamphetamine sulfate one hour after the intraperitoneal administration of the test compound.

The mortality per group was totally counted 4 hours after the administration of dexamphetamine sulfate and the $DE_{50}$ dose which reduced by 50% the number of dead animals was determined as shown in Table I.

TABLE I

| Compound of Example | $DE_{50}$ in mg/kg |
| --- | --- |
| 6 | 35 |
| 7 | 20 |
| 9 | 50 |

The results of Table I show that the compounds, particularly those of Examples 6 and 7, exercise an important antagonism with respect to the toxicity of the amphetamine group.

2. Potentialization of sleeping time

This test was effected with amytal (5-ethyl-5-isoamyl-barbituric acid) on groups of female mice weighing 18 to 22 g and held at 25° C for the duration of the test. The test products were administered intraperitoneally at different does one hour before the intravenous administration of 80 mg/kg of amytal and the time of sleep was recorded as the suspending time for the straighting reflex of the mice as negative. The minimum dose for significantly prolonging the duration of sleep was determined and the results are reported in Table II.

TABLE II

| Product of Example | $DE_{50}$ in mg/kg |
| --- | --- |
| 1 | 10 |
| 2 | 50 |
| 4 | 50 |
| 5 | 50 |
| 6 | 20 |
| 7 | 10 |

The results of Table II show that the products tested, particularly Examples 1 and 7, possess a very important neurosedative activity.

3. Antagonism to reserpinic rigidity

This test was effected on rats using the procedure of Jurna I. [Arch. Pharmak. Exp. Path., Vol. 260 (1968), p. 80–88] wherein the electromyogram (EMG) caused by a dorsiflexion due to the shock of the foot by electrodes placed against the muscles of the front portion of the rear paw of the animal. A dose of 10 mg/kg of reserpine was intravenously administered and then 30 minutes later when the hypertonicity of the muscle was the maximum, the test product was intravenously administered at a dose of 20 mg/kg. The inhibition was observed by the electromyogram showing the antagonism exercised by the test product against the rigidity provoked by reserpine. The results were expressed by an increasing number of + sign and the results are reported in Table III.

TABLE III

| Compound of Example | Antagonism to reserpine rigidity |
|---|---|
| 1 | ++ |
| 3 | + |
| 5 | ++ |

The results show that the products of Examples 1 and 5 are particularly very active at a dose of 20 mg/kg

B. Antiserotonine Activity

Serotonine provokes contraction of a certain number of smooth muscles and especially guinea pig ileon and antiserotonine activity is determined in vitro on the isolated ileon of the guinea pig immersed in oxygenated Tyrode liquid at 37° C. The activity of the antagonist is measured by the concentration thereof which after a contact time of one minute diminishes by about 50% the contraction of a portion of ileon when a standard dose of serotonine is added to the Tyrode liquid. The approximate 50% inhibiting concentration ($IC_{50}$) was determined in micrograms per ml and the results are in Table IV.

TABLE IV

| Products of Examples | $IC_{50}$ micrograms/ml |
|---|---|
| 1 | 0.5 |
| 2 | 0.5 - 1 |
| 3 | 1 |
| 5 | 2 |
| 6 | 2 |
| 7 | 1 - 2 |
| 9 | 0.1 - 0.2 |

The results of Table IV show that the products possess an important antiserotonine activity, particularly the product of Example 9.

C. Platelet Aggegation

Platelet aggregation is effected with a Mustard aggregometer using the turbidimetric method of Born [J. Physiol., Vol. 168 (1963), p. 178–195] which consists of measuring the variation in transmission of a light ray or beam passing through a tube containing a plasma rich in platelets. When the aggregates are formed, the amount of light transmitted is greater and the optical density is diminished. The platelets used are obtained from rabbit plasma and the agent inducing the aggregation was 40 μg/ml of collagen. The 50% inhibiting concentration ($IC_{50}$) was determined for each product which was the dose which inhibited by 50% the aggregation caused by collagen. The results are reported in Table V.

TABLE V

| Products of Examples | $IC_{50}$ in M/l |
|---|---|
| 5 | $\approx 10^{-4}$ |
| 6 | $10^{-5}$ to $10^{-6}$ |
| 9 | $10^{-6}$ |

The results of Table V show that the products have an important activity against platelet aggregation caused by collagen, particularly the products of Examples 6 and 9.

D. Acute toxicity

The 50% lethal dose ($DL_{50}$) was determined by intraperitoneal administration of the products to mice and the mortality was determined 48 hours later. The results are reported in Table VI.

TABLE VI

| Product of Examples | Approximate $DL_{50}$ in mg/kg |
|---|---|
| 1 | 150 |
| 2 | 200 |
| 3 | 350 |
| 4 | 500 |
| 5 | 150 |
| 6 | 150 |
| 7 | 150 |
| 10 | 300 |

Various modifications of the products and processes of the invention may be made without departing from the spirit or scope thereof and it should be understood that the invention is intended to be limited only as defined in the appended claims.

We claim:

1. A compound selected from the group consisting of compounds of the formula

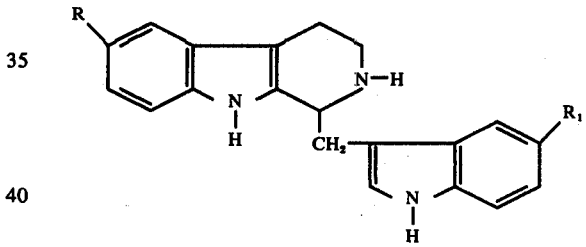

wherein R and $R_1$ are individually selected from the group consisting of hydrogen, halogen, hydroxy, alkoxy of 1 to 5 carbon atoms and benzyloxy with the proviso that $R_1$ is not hydroxy when R is halogen, alkoxy or benzyloxy and their non-toxic, pharmaceutically acceptable acid addition salts.

2. A compound of claim 1 wherein R and $R_1$ are individually selected from the group consisting of hydrogen, chlorine, hydroxy, methoxy and benzyloxy with the proviso that $R_1$ is not hydroxy when R is chlorine, methoxy or benzyloxy.

3. A compound selected from the group consisting of 1-(5'-methoxy-3'-indolyl-methyl)-6-methoxy-1,2,3,4-tetrahydro-[9H]-pyrido-[3,4-b]-indole and its hydrochloride.

4. A compound selected from the group consisting of 1-(5'-methoxy-3'-indolyl-methyl)-1,2,3,4-tetrahydro-[9H]-pyrido-[3,4-b]-indole and its hydrochloride.

5. A compound selected from the group consisting of 6-hydroxy-1-(3'-indolyl-methyl)-1,2,3,4-tetrahydro-[9H]-pyrido-[3,4-b]-indole and its fumarate.

6. A compound selected from the group consisting of 6-chloro-1-(3'-indolyl-methyl)-1,2,3,4-tetrahydro-[9H]-pyrido-[3,4-b]-indole and its hydrochloride.

7. A compound selected from the group consisting of 1-(5'-hydroxy-3'-indolyl-methyl)-1,2,3,4-tetrahydro-[9H]-pyrido-[3,4-b]-indole and its hydrochloride.

8. A process for the preparation of a compound of claim 1 wherein $R_1$ is selected from the group consisting of hydrogen, halogen, alkoxy of 1 to 5 carbon atoms and benzyloxy comprising reacting a tryptamine of the formula

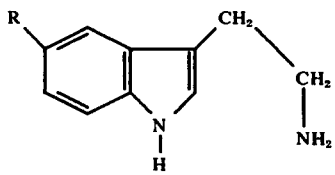

with a 3-indole pyruvic acid of the formula

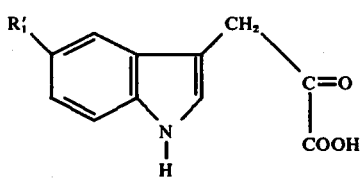

wherein $R_1'$ is selected from the group consisting of hydrogen, halogen, alkoxy of 1 to 5 carbon atoms and benzyloxy to obtain a compound of the formula

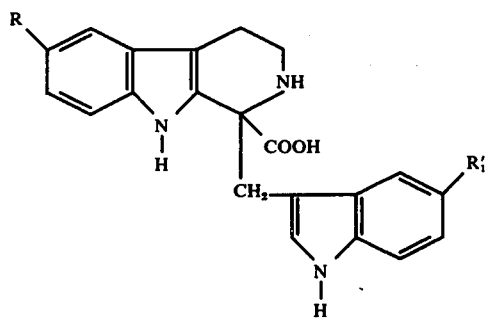

and decarboxylating the latter to form the corresponding compound of claim 1.

9. A process for the preparation of a compound of claim 1 wherein R is selected from the group consisting of hydrogen and benzyloxy and $R_1$ is benzyloxy or R is selected from the group consisting of hydrogen and hydroxy and $R_1$ is hydroxy comprising reacting a tryptamine of the formula

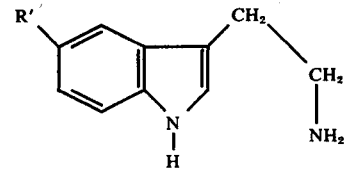

wherein R' is hydrogen or benzyloxy with a product of the formula

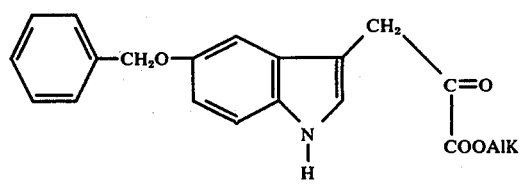

wherein AlK is alkyl of 1 to 3 carbon atoms to form a compound of the formula

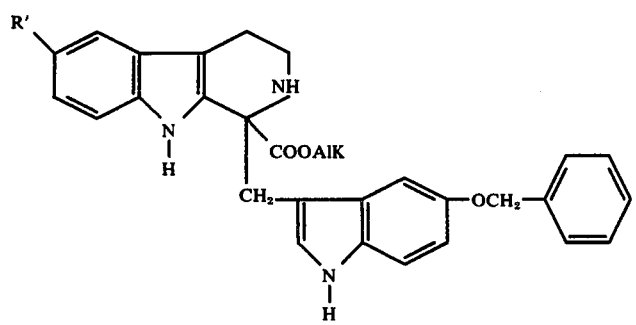

which is then hydrolyzed and decarboxylated, and which is hydrogenolyzed when it is desired to obtain a compound in which R is hydrogen or hydroxy and $R_1$ is hydroxy, to form a compound of claim 1 wherein R and $R_1$ have the above definition.

10. A tranquillizing composition comprising an effective amount of at least one compound of claim 1 and an inert pharmaceutical carrier.

11. A composition of claim 10 wherein the active compound is 1-(5'-hydroxy-3'-indolyl-methyl)-1,2,3,4-tetrahydro-[9H]-pyrido-[3,4-b]-indole-hydrochloride.

12. A method of tranquillizing warm-blooded animals comprising administering to warm-blooded animals a tranquillizingly effective amount of at least one compound of claim 1.

13. The method of claim 12 wherein the active compound is 1-(5'-hydroxy-3'-indolyl-methyl)-1,2,3,4-tetrahydro-[9H]-pyrido-[3,4-b]-indole-hydrochloride.

* * * * *